(12) United States Patent
Glover

(10) Patent No.: US 10,408,770 B2
(45) Date of Patent: Sep. 10, 2019

(54) VIDEO BORESCOPE DEVICE

(71) Applicant: George Glover, Katy, TX (US)

(72) Inventor: George Glover, Katy, TX (US)

(*) Notice: Subject to any disclaimer, the term of this patent is extended or adjusted under 35 U.S.C. 154(b) by 69 days.

(21) Appl. No.: 15/692,386

(22) Filed: Aug. 31, 2017

(65) Prior Publication Data

US 2019/0064080 A1 Feb. 28, 2019

(51) Int. Cl.
*G01N 21/954* (2006.01)
*H04N 7/18* (2006.01)
*G02B 23/24* (2006.01)
*H04N 5/225* (2006.01)

(52) U.S. Cl.
CPC ....... *G01N 21/954* (2013.01); *G02B 23/2484* (2013.01); *H04N 5/2257* (2013.01); *H04N 7/183* (2013.01); *G02B 23/2469* (2013.01); *H04N 5/2256* (2013.01); *H04N 2005/2255* (2013.01)

(58) Field of Classification Search
CPC ......... H04N 2005/2255; H04N 5/2251; H04N 5/2256; H04N 57/183; G01N 21/954; G02B 23/2484; G02B 23/2469
See application file for complete search history.

(56) References Cited

U.S. PATENT DOCUMENTS

| | | |
|---|---|---|
| D277,505 S | 2/1985 | Kubokawa et al. |
| 4,919,114 A | 4/1990 | Miyazaki |
| 6,091,453 A | 7/2000 | Coan et al. |
| 6,683,641 B1* | 1/2004 | MacCracken ........... F01D 5/005 348/82 |
| 6,747,394 B2 | 6/2004 | Johansson et al. |
| 8,659,652 B2 | 2/2014 | Schneider et al. |
| 2004/0160514 A1* | 8/2004 | Tawfig ................ E21B 47/0002 348/85 |
| 2006/0043303 A1* | 3/2006 | Safai .................. G01N 21/9515 250/347 |
| 2009/0073271 A1* | 3/2009 | Grenlund ............. H04N 5/2251 348/211.8 |
| 2009/0167851 A1* | 7/2009 | Miller ................ G02B 23/2476 348/82 |
| 2014/0182373 A1* | 7/2014 | Sbihli .................. G01N 27/902 73/488 |
| 2015/0338353 A1* | 11/2015 | Bancalari ............. F01D 21/003 348/82 |

(Continued)

FOREIGN PATENT DOCUMENTS

WO WO2014150055 9/2014

*Primary Examiner* — Amy R Hsu

(57) ABSTRACT

A video borescope device for visualizing hard to reach spaces includes a tube that is flexible and configured to insert into a space, such as defined by an engine. A camera is coupled to a first end of the tube and is operationally coupled to the optical relay that is positioned in the tube. A coupler that is coupled to a second end of the tube is configured to operationally couple the optical relay to a computer. A plurality of bulbs that is coupled to the first end of the tube is configured to provide illumination. Programming code that is positioned on the computer enables a user to compel the camera to capture an image, such as a still picture and a video, and to transfer the image to the optical relay. The optical relay is positioned to relay the image to the computer to present on a display.

13 Claims, 5 Drawing Sheets

(56) References Cited

U.S. PATENT DOCUMENTS

| | | | |
|---|---|---|---|
| 2016/0072991 A1* | 3/2016 | Dinev | H04N 5/2256 |
| | | | 348/370 |
| 2016/0095507 A1 | 4/2016 | Uram et al. | |
| 2017/0031492 A1* | 2/2017 | Coombs | G06F 3/005 |
| 2017/0330665 A1* | 11/2017 | Zareei | H01F 7/064 |

* cited by examiner

VIDEO BORESCOPE DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention
(2) Description of Related Art Including Information Disclosed Under 37 CFR 1.97 and 1.98.

The disclosure and prior art relates to borescope devices and more particularly pertains to a new borescope device for visualizing hard to reach spaces.

BRIEF SUMMARY OF THE INVENTION

An embodiment of the disclosure meets the needs presented above by generally comprising a tube that is flexible and configured to insert into a space, such as defined by an engine. A camera is coupled to a first end of the tube and is operationally coupled to the optical relay that is positioned in the tube. A coupler that is coupled to a second end of the tube is configured to operationally couple the optical relay to a computer. A plurality of bulbs that is coupled to the first end of the tube is configured to provide illumination. Programming code that is positioned on the computer enables a user to compel the camera to capture an image, such as a still picture and a video, and to transfer the image to the optical relay. The optical relay is positioned to relay the image to the computer to present on a display.

There has thus been outlined, rather broadly, the more notable features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
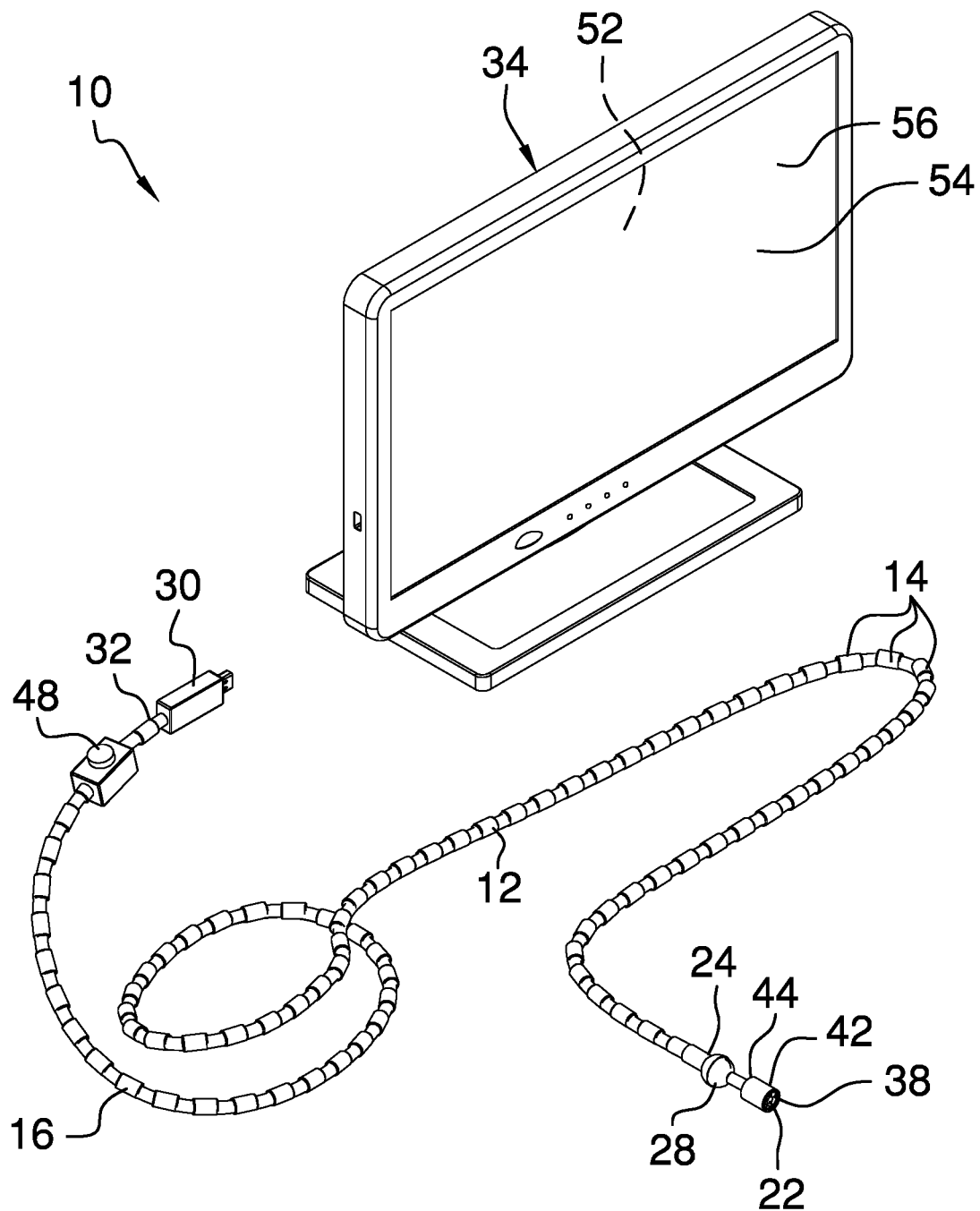
FIG. 1 is an isometric perspective view of a video borescope device according to an embodiment of the disclosure.
Figure 2:
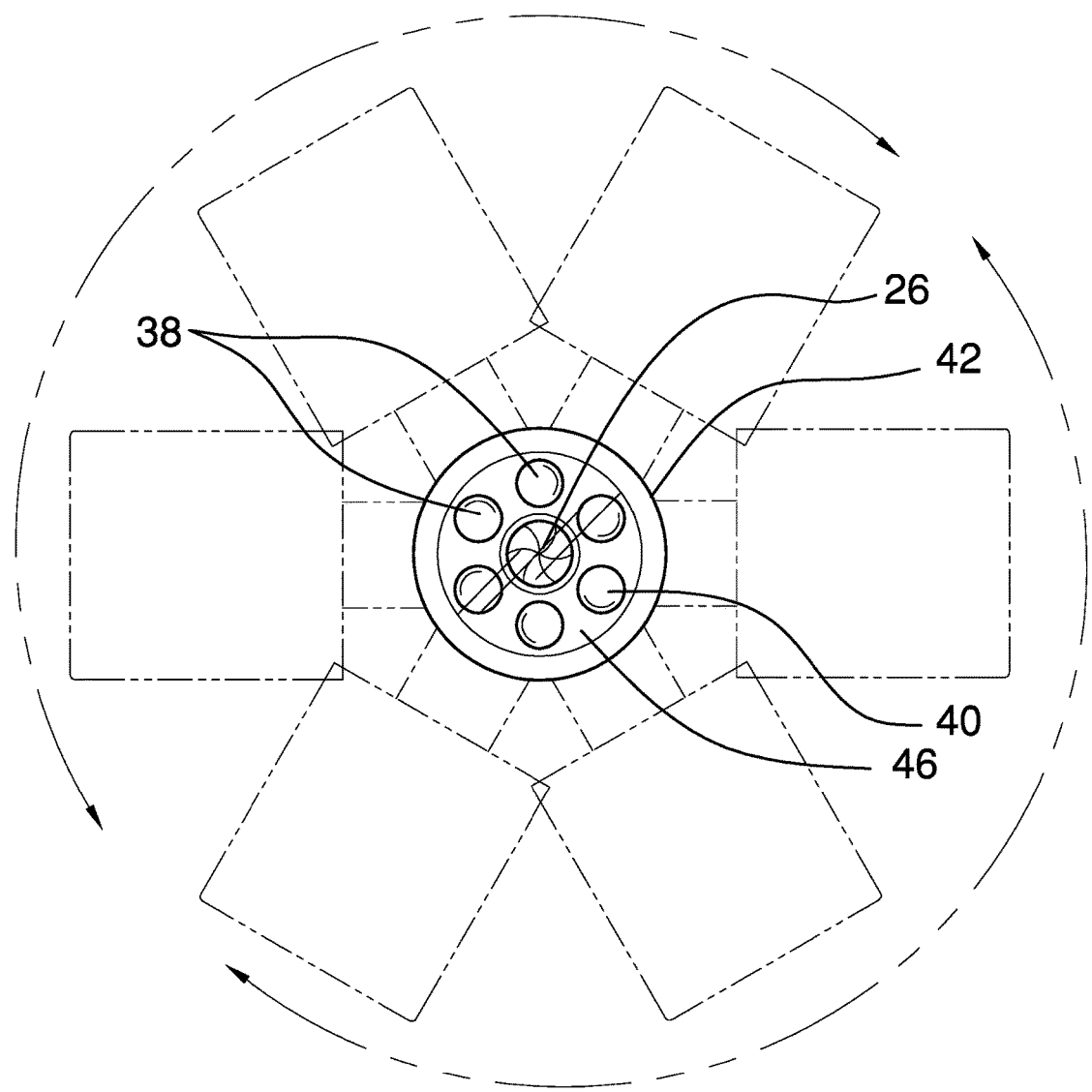
FIG. 2 is a front view of an embodiment of the disclosure.
Figure 3:
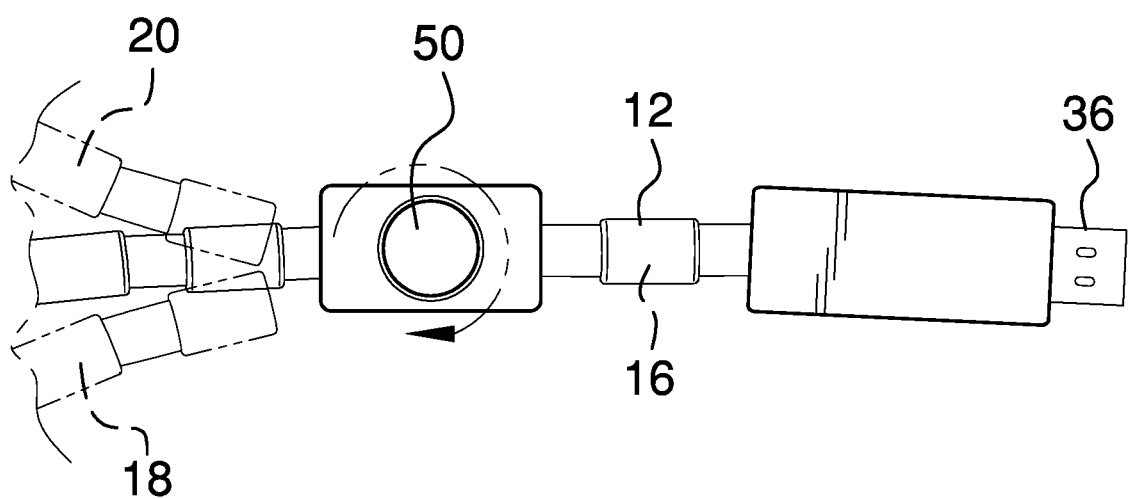
FIG. 3 is a side view of an embodiment of the disclosure.
Figure 4:
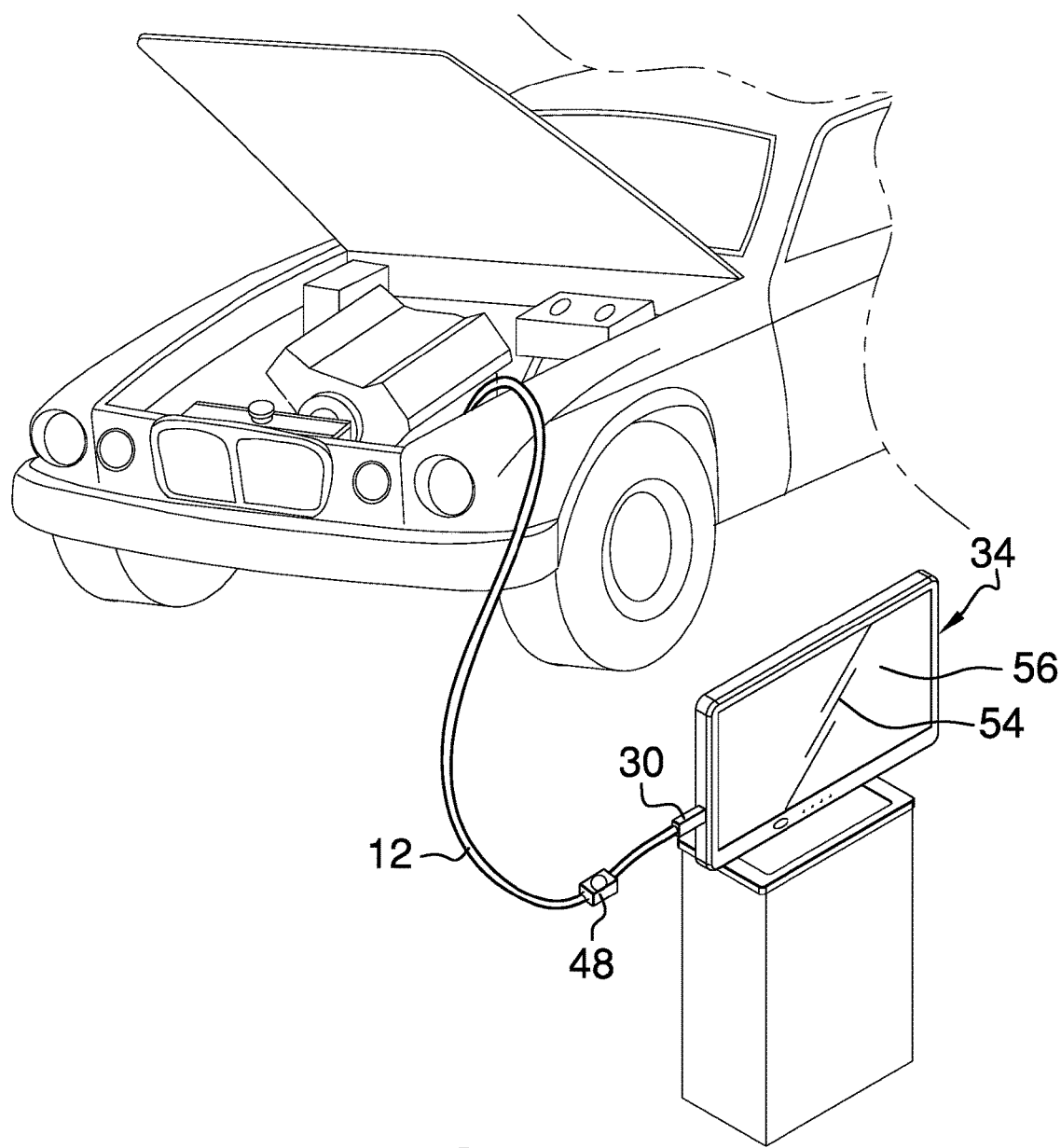
FIG. 4 is an in-use view of an embodiment of the disclosure.
Figure 5:
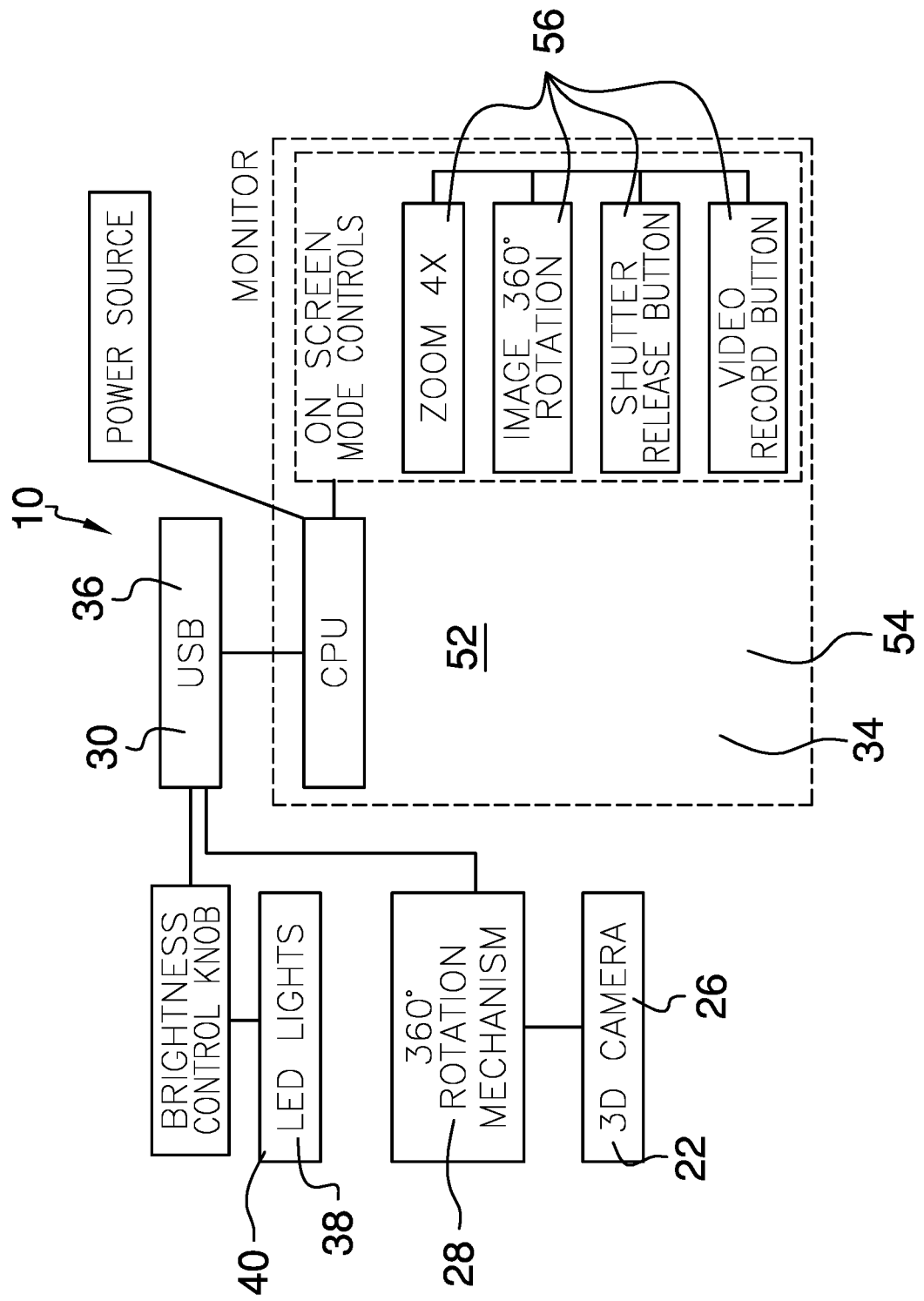
FIG. 5 is a block diagram of an embodiment of the disclosure.

With reference now to the drawings, and in particular to FIGS. 1 through 5 thereof, a new borescope device embodying the principles and concepts of an embodiment of the disclosure and generally designated by the reference numeral 10 will be described.

As best illustrated in FIGS. 1 through 5, the video borescope device 10 generally comprises a tube 12 that is flexible. The tube 12 is configured to insert into a space, such as defined by an engine, piping, and tubing. The tube 12 is waterproof. In one embodiment, the tube 12 comprises a plurality of interconnected sections 14. Each interconnected section 14 is selectively angularly positionable relative to adjacently positioned interconnected sections 14.

An optical relay 16 and an articulation system 20 are positioned in the tube 12. In one embodiment, the optical relay 16 comprises a plurality of optical fibers 18. The articulation system 20 is operationally coupled to the plurality of interconnected sections 14. The articulation system 20 is positioned to compel a respective three-dimensional configuration of the tube 12.

A camera 22 is coupled to a first end 24 of the tube 12. The camera 22 is operationally coupled to the optical relay 16. The camera 22 is positioned to capture an image, such as a still picture and a video, and to transfer the image to the optical relay 16. In one embodiment, the camera 22 comprises a plurality of microlenses 26. The microlenses 26 are configured to capture the image and to focus the image on the plurality of optical fibers 18. In another embodiment, the camera 22 is configured to capture the image in three dimensions.

An actuator 28 is positioned between the camera 22 and the first end 24 of the tube 12. The actuator 28 is positioned to selectively compel rotation of the camera 22 relative to the tube 12.

A coupler 30 is coupled to a second end 32 of the tube 12. The coupler 30 is positioned to operationally couple the optical relay 16 to a computer 34. In one embodiment, the coupler 30 comprises a male universal serial bus connector 36.

A plurality of bulbs 38 is coupled to the first end 24 of the tube 12. The bulbs 38 are configured to provide illumination. In one embodiment, the plurality of bulbs 38 comprises six bulbs 38 that are positioned circularly around the camera 22. In another embodiment, each bulb 38 comprises a light emitting diode 40. In yet another embodiment, the light emitting diode 40 is configured to emit pure super bright cold white light.

A cylinder 42 is coupled to and extends from the actuator 28. The cylinder 42 has a top 44 that is positioned proximate to the actuator 28. The top 44 is closed. The cylinder 42 has a base 46 that is open. The camera 22 and the plurality of bulbs 38 are positioned in the cylinder 42. The cylinder 42 is configured to shield the camera 22 and the bulbs 38.

A controller 48 is coupled to the tube 12 proximate to the second end 32. The controller 48 is operationally coupled to the plurality of bulbs 38. The controller 48 is positioned to selectively compel the plurality of bulbs 38 to provide a respective degree of illumination. In one embodiment, the controller 48 comprises a knob 50. The knob 50 is rotatable relative to the tube 12. The knob 50 is positioned to be rotated to selectively compel the plurality of bulbs 38 to provide the respective degree of illumination.

Programming code 52 is positioned on the computer 34 to enable a user to compel the camera 22 to capture the image. The optical relay 16 is positioned to relay the image to the computer 34. The computer 34 is positioned to present the image on a display 54 that is operationally coupled to the computer 34. In one embodiment, the display 54 is touch enabled. The programming code 52 comprises programming code 52 to compel the display 54 to present a plurality of control buttons 56 on the display 54. Each control button 56 is configured to be touched by the user to control a respective function, such as to compel the articulation system 20 to compel the respective three-dimensional configuration of the tube 12, to compel the actuator 28 to compel a respective rotational position of the camera 22 relative to the tube 12, to compel the camera 22 to set a magnification level of the image, and to compel the camera 22 to capture the image.

In use, the tube 12 is configured to insert into a space, such as defined by the engine, the piping, and the tubing. The articulation system 20 that is positioned in the tube 12 is positioned to compel the respective three-dimensional configuration of the tube 12. The bulbs 38 that are positioned on the tube 12 are configured to provide illumination. The microlenses 26 that are positioned on the tube 12 are configured to capture the image and to focus the image, such as the still picture and the video, on the plurality of optical fibers 18. The optical fibers 18 are positioned to relay the image to the computer 34. The computer 34 is positioned to present the image on the display 54. The control buttons 56 are presented on the display 54 so that each control button 56 is configured to be touched by the user to control the respective function, such as to compel the articulation system 20 to compel the respective three-dimensional configuration of the tube 12, to compel the actuator 28 to compel the respective rotational position of the camera 22 relative to the tube 12, to compel the camera 22 to set the magnification level of the image, and to compel the camera 22 to capture the image.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A video borescope device comprising:

a tube, said tube being flexible such that said tube is configured for inserting into a space, said tube comprising a plurality of interconnected sections, each said interconnected section being selectively angularly positionable relative to adjacently positioned said interconnected sections;

an articulation system positioned in said tube, said articulation system being operationally coupled to said plurality of interconnected sections, wherein said articulation system is positioned in said tube such that said articulation system is positioned for compelling a respective three-dimensional configuration of said tube;

an optical relay positioned in said tube;

a camera coupled to a first end of said tube, said camera being operationally coupled to said optical relay;

an actuator positioned between said camera and said first end of said tube, said actuator being configured for selectively compelling rotation of said camera relative to said tube, wherein said actuator is positioned on said tube such that said actuator is positioned for compelling rotation of said camera relative to said tube;

a coupler coupled to a second end of said tube, said coupler being configured for operationally coupling said optical relay to a computer;

a plurality of bulbs coupled to said first end of said tube;

a cylinder coupled to and extending from said actuator, said cylinder having a top positioned proximate to said actuator, said top being closed, said cylinder having a base, said base being open, said camera and said plurality of bulbs being positioned in said cylinder wherein said base is unobstructed to define a planar terminal end of said cylinder, wherein said cylinder is positioned on said actuator such that said cylinder is configured for shielding said camera and said bulbs;

programming code positioned on said computer for enabling a user for compelling said camera for capturing an image such that said optical relay is positioned for relaying the image to said computer such that said computer is positioned for presenting the image on a display operationally coupled to said computer; and wherein said tube is configured for inserting into a space, wherein said bulbs are positioned on said tube such that said bulbs are configured for providing illumination, wherein said camera is positioned on said tube such that said camera is positioned for capturing the image, and for transferring the image to said optical relay, such that said computer is positioned for presenting the image on the display.

2. The device of claim 1, further including said tube being waterproof.

3. The device of claim 1, further including said optical relay comprising a plurality of optical fibers.

4. The device of claim 1, further including said camera comprising a plurality of microlenses, wherein said microlenses are positioned on said tube such that said microlenses are configured for capturing the image and for focusing the image on said plurality of optical fibers.

5. The device of claim 1, further including said camera being configured for capturing the image in three dimensions.

6. The device of claim 1, further including said coupler comprising a male universal serial bus connector.

7. The device of claim 1, further including said plurality of bulbs comprising six said bulbs positioned circularly around said camera.

8. The device of claim 1, further including each said bulb comprising a light emitting diode.

9. The device of claim 8, further including said light emitting diode being configured for emitting pure super bright cold white light.

10. The device of claim 1, further including a controller coupled to said tube proximate to said second end, said controller being operationally coupled to said plurality of bulbs, wherein said controller is positioned on said tube such that said controller is positioned for selectively compelling said plurality of bulbs for providing a respective degree of illumination.

11. The device of claim 10, further including said controller comprising a knob, said knob being rotatable relative to said tube, wherein said knob is positioned on said tube such that said knob is positioned for rotating for selectively compelling said plurality of bulbs for providing the respective degree of illumination.

12. The device of claim 1, further including said display being touch enabled, said programming code comprising programming code for compelling said display for presenting a plurality of control buttons on said display, wherein said control buttons are presented on said display such that each said control button is configured for touching by the user for controlling a respective function, such as for compelling the articulation system for the respective three-dimensional configuration of said tube, for compelling said actuator for a respective rotational position of said camera relative to said tube, for compelling said camera for a magnification level of the image, and for compelling said camera for capturing the image.

13. A video borescope device comprising:
a tube, said tube being flexible such that said tube is configured for inserting into a space, said tube being waterproof, said tube comprising a plurality of interconnected sections, each said interconnected section being selectively angularly positionable relative to adjacently positioned said interconnected sections;
an optical relay positioned in said tube, said optical relay comprising a plurality of optical fibers;
an articulation system positioned in said tube, said articulation system being operationally coupled to said plurality of interconnected sections, wherein said articulation system is positioned in said tube such that said articulation system is positioned for compelling a respective three-dimensional configuration of said tube;
a camera coupled to a first end of said tube, said camera being operationally coupled to said optical relay, wherein said camera is positioned on said tube such that said camera is positioned for capturing an image and for transferring the image to said optical relay, said camera comprising a plurality of microlenses, wherein said microlenses are positioned on said tube such that said microlenses are configured for capturing the image and for focusing the image on said plurality of optical fibers, said camera being configured for capturing the image in three dimensions;
an actuator positioned between said camera and said first end of said tube, said actuator being configured for selectively compelling rotation of said camera relative to said tube, wherein said actuator is positioned on said tube such that said actuator is positioned for compelling rotation of said camera relative to said tube;
a coupler coupled to a second end of said tube, said coupler being configured for operationally coupling said optical relay to a computer, said coupler comprising a male universal serial bus connector;
a plurality of bulbs coupled to said first end of said tube, wherein said bulbs are positioned on said tube such that said bulbs are configured for providing illumination, said plurality of bulbs comprising six said bulbs positioned circularly around said camera, each said bulb comprising a light emitting diode, said light emitting diode being configured for emitting pure super bright cold white light;
a cylinder coupled to and extending from said actuator, said cylinder having a top positioned proximate to said actuator, said top being closed, said cylinder having a base, said base being open, said camera and said plurality of bulbs being positioned in said cylinder wherein said base is unobstructed to define a planar terminal end of said cylinder, wherein said cylinder is positioned on said actuator such that said cylinder is configured for shielding said camera and said bulbs;
a controller coupled to said tube proximate to said second end, said controller being operationally coupled to said plurality of bulbs, wherein said controller is positioned on said tube such that said controller is positioned for selectively compelling said plurality of bulbs for providing a respective degree of illumination, said controller comprising a knob, said knob being rotatable relative to said tube, wherein said knob is positioned on said tube such that said knob is positioned for rotating for selectively compelling said plurality of bulbs for providing the respective degree of illumination;
programming code positioned on said computer for enabling a user for compelling said camera for capturing the image such that said optical relay is positioned for relaying the image to said computer such that said computer is positioned for presenting the image on a display operationally coupled to said computer, said display being touch enabled, said programming code comprising programming code for compelling said display for presenting a plurality of control buttons on said display, wherein said control buttons are presented on said display such that each said control button is configured for touching by the user for controlling a respective function, such as for compelling the articulation system for the respective three-dimensional configuration of said tube, for compelling said actuator for a respective rotational position of said camera relative to said tube, for compelling said camera for a magnification level of the image, and for compelling said camera for capturing the image; and
wherein said tube is configured for inserting into a space, wherein said articulation system is positioned in said tube such that said articulation system is positioned for compelling the respective three-dimensional configuration of said tube, wherein said bulbs are positioned on said tube such that said bulbs are configured for providing illumination, wherein said microlenses are positioned on said tube such that said microlenses are configured for capturing the image and for focusing the image, such as the still picture and the video, on said plurality of optical fibers, such that said optical fibers are positioned for relaying the image to said computer, such that said computer is positioned for presenting the image on the display, wherein said control buttons are presented on said display such that each said control button is configured for touching by the user for controlling the respective function including for compelling the articulation system for the respective three-dimensional configuration of said tube, for compelling said actuator for the respective rotational position of said camera relative to said tube, for compelling said camera for the magnification level of the image, and for compelling said camera for capturing the image.

* * * * *